(12) United States Patent
Choong et al.

(10) Patent No.: US 6,238,909 B1
(45) Date of Patent: May 29, 2001

(54) METHOD AND APPARATUS FOR OBTAINING ELECTRIC FIELD-ENHANCED BIOCONJUGATION

(75) Inventors: Vi-En Choong, Chandler; George Maracas; Larry Akio Nagahara, both of Phoenix, all of AZ (US)

(73) Assignee: Motorola, Inc., Northbrook, IL (US)

(*) Notice: Subject to any disclaimer, the term of this patent is extended or adjusted under 35 U.S.C. 154(b) by 0 days.

(21) Appl. No.: 09/305,163

(22) Filed: May 4, 1999

(51) Int. Cl.[7] ............................. C12Q 1/68; C12M 1/34; G01N 33/00
(52) U.S. Cl. ........................... 435/287.2; 435/6; 436/94
(58) Field of Search ................. 435/6, 91.1, 91.2, 435/287.2; 436/94, 501; 530/350; 536/23.1, 24.3; 472/68.1

(56) References Cited

U.S. PATENT DOCUMENTS

| | | | |
|---|---|---|---|
| 5,059,294 | * | 10/1991 | Lizardi et al. . |
| 5,532,128 | * | 7/1996 | Eggers et al. . |
| 5,565,322 | * | 10/1996 | Heller et al. . |
| 5,605,662 | * | 2/1997 | Heller et al. ................. 422/68.1 |
| 5,632,957 | * | 5/1997 | Heller et al. ................. 422/68.1 |
| 5,653,939 | * | 8/1997 | Hollis et al. . |
| 5,728,532 | * | 3/1998 | Ackley . |
| 5,929,208 | * | 7/1999 | Heller et al. .................. 530/333 |

FOREIGN PATENT DOCUMENTS

| | | |
|---|---|---|
| WO 93/22678 | * 11/1993 | (WO) . |
| WO 98/08082 | * 2/1998 | (WO) . |
| WO 98/10273 | * 3/1998 | (WO) . |

OTHER PUBLICATIONS

Washizu, "Electrostatic manipulation of biological objects", *Journal of Electrostatics*, 25, 109–123 (1990).*

* cited by examiner

*Primary Examiner*—Bradley L. Sisson
(74) *Attorney, Agent, or Firm*—Flehr Hohbach Test Albritton & Herbert LLP; Robin M. Silva (57) ABSTRACT

Among other things, the invention provides devices and methods for obtaining electric field-enhanced bioconjugation events. In particular, the invention provides for contactless electrodes for obtaining the electric field, such that transport and bioconjugation of charged molecules is obtained in the absence of current flow through the buffer, sample, and/or porous media.

14 Claims, 1 Drawing Sheet

FIG._3

METHOD AND APPARATUS FOR OBTAINING ELECTRIC FIELD-ENHANCED BIOCONJUGATION

TECHNICAL FIELD OF THE INVENTION

The present invention provides, among other things, devices and methods for obtaining electric field-enhanced bioconjugation events. In particular, the invention provides so-called "contactless electrodes" for obtaining the electric field, and for effecting transport and bioconjugation of charged molecules in the absence of current flow through the buffer, sample, and/or porous media.

BACKGROUND OF THE INVENTION

Current demand in the biotechnological, chemical, and medical arts, is for inexpensive, effective, and streamlined devices for carrying out rapid analysis of samples to determine composition, either in toto (e.g., full sample sequencing), at a specific site (e.g., sequencing at a queried base), and/or in terms of ability to interact with (e.g., hybridize to) a reference molecule such as a nucleic acid. The devices must be flexible, and optionally perform a variety of actions, e.g., nucleic acid hybridization, antibody/antigen reactions, diagnostics, biopolymer synthesis, and the like.

Several patents in the prior art concern active programmable electronic devices for molecular biological analysis and diagnostics, e.g., U.S. Pat. Nos. 5,605,662, 5,632,957, and 5,565,322. These patents employ full contact electrodes (i.e., electrodes that are placed in contact with sample and/or buffer, and effect movement of molecules by electrophoretic transport.

Similarly, U.S. Pat. No. 5,532,128, discloses a method and apparatus for identifying molecular structures within a sample substance using an array having a plurality of test sites upon which the sample substance is applied. According to this patent, a first electrode and second electrode are disposed "adjacent" to a test site to form a capacitor in conjunction with the test substance. This consequently results in a plurality of electrodes associated with the test site, with each test site having at least one electrode attached to it for electrical coupling with a second electrode. According to this patent, hybridization is carried out by standard means. The electrodes are employed after hybridization to determine if there has been a change in the properties of the probe at the test site due to sample hybridization with probe.

In U.S. Pat. No. 5,653,939, the electrodes also are side-by-side, or adjacent. Consequently, this device is difficult to construct, and requires precise interdigitized electrodes. Construction of the device requires a metallization step, and the device is not readily accessible to probe construction (probe deposition). Moreover, the electrodes in this device necessarily are "full contact" electrodes, where the electrodes are in contact with (i.e., physically touch) with the buffer in which the sample is contained (e.g., see FIG. 4).

U.S. Pat. No. 5,059,294 discloses an improved method and device for carrying out a nucleic acid hybridization assay which employs combined direct and alternating field electrophoresis. In this method, a sample is hybridized with nucleic acid probe and contacted with a support medium where direct and alternating electric fields are applied. Under the influence of the electric fields, hybrid separates from nonspecifically bound nucleic acid probe. Thus, the alternating current and direct current are applied to the support medium merely to disrupt non-specific binding and cause separation, not to facilitate hybridization. Furthermore, it is necessary for this invention that the support medium is capable of conducting electric current.

By comparison, U.S. Pat. No. 5,728,532 (and PCT International Application WO 98/082082) discloses an apparatus and method for selectively attracting and inhibiting attraction of at least one predetermined molecule to a site in a molecular detection device, where the device makes use of a first electrode and a second electrode proximate to the site (as well as a third electrode to produce a bias). The first electrode selectively generates a first electric field proximate to the site in response to a first signal applied to the site. The first electric field provides an attractive force to attract at least one predetermined molecule toward the site. The second electrode selectively generates a second electric field proximate to the site in response to a second signal applied to the site. The second electric field selectively inhibits attraction of a second predetermined molecule (i.e., at least one) toward the site by providing a repulsive force which dominates the attractive force provided by the first electric field. The electrodes employed according to this patent are full contact electrodes.

Thus, there remains a need for a device that has certain advantages over those previously described. First, it would be desirable for such a device to not need to be restricted in terms of the material of the electrode to only biocompatible materials (i.e., restricted because the electrodes come into contact with the sample or buffer). Second, it would be desirable if such a device could eliminate the need for complicated designs, and micro- and nano-lithography to incorporate the electrodes (e.g., full contact electrodes) in the array. Third, it would be desirable if such a device could avoid any unwanted or unexpected reaction between the electrodes and the sample, or between the electrodes and the buffer solution. Also, it would be preferable if such a device could eliminate the probability of electrode degradation, and unwanted current flow.

The preferred devices according to the invention optimally possesses these characteristics. The devices and methods of the invention provide increased flexibility in electrode material selection, desirably by eliminating direct physical contact between the electrode and buffer (as well as between the electrode and sample). These and other objects and advantages of the present invention, as well as additional inventive features, will be apparent from the description of the invention provided herein.

BRIEF SUMMARY OF THE INVENTION

The invention pertains to devices and methods for obtaining electric field-enhanced bioconjugation events. The devices and methods preferably employ contactless electrodes for obtaining the electric field.

DETAILED DESCRIPTION OF THE PREFERRED EMBODIMENTS

The invention provides, among other things, devices (e.g., electronic or other types of devices) and methods for obtaining electric field-enhanced bioconjugation events. The devices and methods preferably employ two or more electrodes for obtaining the electric field, wherein the electrodes are so-called "contactless electrodes".

Thus, the invention provides a preferred device adapted for bioconjugation, wherein the device desirably comprises:

(a) a substrate;

(b) one or a plurality of microlocation(s) present on the substrate;

(c) a buffer present on or surrounding the microlocation(s);

(d) two or more electrodes adapted to receive charge, the two or more electrodes being separated from one another, from the microlocation(s), and from the buffer, but appropriately positioned so as to create an electric field in the microlocation(s) without creating current flow in the microlocation(s) when the two or more electrodes receive charge; and (e) a source for providing charge to the electrodes.

In particular, the invention provides a device adapted for the bioconjugation of binding entities, wherein the device desirably comprises:

(a) a substrate;

(b) one or a plurality of microlocation(s) present on the substrate, the microlocation(s) each comprising a binding entity;

(c) a source for applying sample comprising one or more further binding entities to the microlocation(s);

(d) a buffer present on or surrounding the microlocation(s);

(e) a first electrode adapted to receive charge;

(f) one or more other electrode(s) adapted to receive charge; and (g) a source for providing charge to the first or the one or more other electrode(s), the first and the one or more other electrode(s) being separated from one another, from the microlocation(s), and from the buffer, but appropriately positioned so as to create an electric field in the microlocation(s) without creating current flow in the microlocations when the two or more electrodes receive charge.

Bioconjugation

By "bioconjugation" or "bioconjugation events" is meant covalent or noncovalent binding of a specific binding entity to another binding entity that is its binding partner. Such bioconjugation events include, but are not limited to, hybridization of polynucleotide species, antibody/antigen binding, chemical association, etc. Preferably, the invention is employed in hybridization, e.g., of polynucleotide species.

By "specific binding entity" desirably is meant a biological or synthetic molecule that has specific chemical attraction or force to another molecule (i.e., to another binding entity), through covalent bonding or non-covalent bonding. Preferably a specific binding entity is one which possesses a charge, and which is able to move in a medium (such as the porous media described herein, with application of a buffer) under the influence of an electric field. The molecule to which the specific binding entity binds (i.e., other binding entity) is a "binding partner", and the molecules combined constitute a "binding pair". Preferably, a specific binding entity contains (either by nature or by modification) a functional chemical group (e.g., a primary amine, sulfhydryl, and aldehyde, to name but a few), a complementary sequence (e.g., a nucleic acid sequence that is complementary to its binding partner), an epitope (including a hapten or a paratope, e.g., in antigen and antibody interactions), or a ligand, that allows it to covalently react or non-covalently bind to a common functional group present on its binding partner. Specific binding entities include, but are not limited to: polynucleotide and oligonucleotide species such as deoxyribonucleic acids (DNA), ribonucleic acids (RNA), and synthetic polynucleotides/oligonucleotides; antibodies; proteins and peptides; lectins; modified polysaccharides; synthetic composite macromolecules; functionalized nanostructures; synthetic polymers; modified/blocked nucleotides/nucleosides; modified/blocked amino acids; fluorophores; chromophores; ligands; chelates; and haptens. Especially preferred binding partners according to the invention include, but are not limited to, a polynucleotide/oligonucleotide species present in a biological sample, and its partner, a polynucleotide/oligonucleotide species that constitutes a probe.

Desirably a specific binding entity constitutes either a molecule of sample, or a molecule of probe.

According to the invention, a "sample" desirably is any sample obtained from any source either natural (i.e., isolated from nature) or synthetic (i.e., synthesized enzymatically in vitro). According to the invention, a sample comprises one or more further binding entities. Desirably a sample comprises sample nucleic acid. The sample nucleic acid preferably comprises deoxyribonucleic acid, ribonucleic acid, a copolymer of deoxyribonucleic acid and ribonucleic acid, and/or protein. The "sample nucleic acid molecule" can be any nucleic acid molecule or molecules, isolated from nature, recombinant, synthetic, or any mixture thereof. Preferably, the sample nucleic acid molecule is a DNA or RNA molecule. The sample comprising the sample nucleic acid molecule can be in any form. In some cases, it may be desirable (but is not necessary) that the sample DNA molecule is present in a form appropriate for amplification by either recombinant (e.g., cell-based) or laboratory (e.g., PCR) means. In particular, preferably the DNA sample comprises the genomic DNA of a human or non-human animal, especially where the DNA is suspected to contain a genetic variation associated with a disease, disorder, or condition (e.g., cancer or human immunodeficiency virus, to name but two), and wherein the method is employed to determine whether the DNA contains the variation.

The sample nucleic acid as employed in the method of the invention desirably is single stranded. A double stranded sample can be rendered single stranded by any means prior to its use in the method. The sample nucleic acid can be taken from any organism. For instance, the sample can be taken from mammals (such as humans, non-human primates, horses, dogs, cows, cats, pigs, or sheep), from viruses, from plants, from microorganisms, from food, from the environment, etc. The present invention provides for analysis of nucleic acid sequences that can be used, for example, in the diagnosis of disease, disorders, or conditions, in the indentification of individuals and their parentage, in veterinary applications (e.g., horse thoroughbred analysis), to name but a few, as well as other applications.

Desirably a "probe" according to the invention is a single stranded oligonucleotide or polynucleotide, or any nucleic acid that can function as a probe as described herein. In some applications (e.g., single base extension), it is desirable that the probe is capable of being extended by the covalent addition of a nucleotide in a template-directed extension reaction (i.e., a reaction in which a polymerase mediates the extension of a primer such that the extended sequence is complementary to the sequence of a nucleic acid template. Thus, for these sorts of applications, it further is desirable that the "probe" function also as a "primer." The sequence of the probe is selected to be complementary to a target polynucleotide, and, in the case of single base extension where the probe also functions as a primer, to be shorter in length than the target polynucleotide whose base identity at a particular sequence location is being determined. According to the invention, the probe/primer desirably is complementary to the region immediately adjacent to, but not including, the target site. Preferably the probe will range from about 1 to about 100 bases in length, desirably from about 1 to about 50 bases in length, especially from about 1 to about 30 bases in length, and particularly from about 1 to about 10 bases in length.

The oligonucleotides or polynucleotides can be purchased as commercially prepared, or chemically synthesized (e.g., on a Cruachem PS 250 DNA Synthesizer, or other automated DNA synthesizer) using standard chemistries (e.g., phosphoramidite chemistry) as discussed, for instance, in Beucage et al., *Tetrahedron*, 48, 2223–2311 (1992), U.S. Pat. Nos. 4,415,732, 4,458,066, 4,725,677, 4,973,679, and 4,980,960. Typically, synthetic oligonucleotides desirably are further purified, e.g., by HPLC followed by a 20% polyacrylamide gel/7 M urea.

Preferably, the DNA probes are present in the array (i.e., as described further below). Desirably the probes are of a known sequence, and are selected to be complementary to the DNA targets present in a sample being assessed.

Substrate and Microlocation(s)

According to the invention, bioconjugation desirably is carried in a porous media. A "porous media" is any media that allows molecules (e.g., binding entities) to move freely through it, and through which an electric field can be propagated (e.g., preferably in the absence of accompanying current flow through the porous media).

Such porous media (e.g., depicted as "20" in FIGS. 1–3) includes, but is not limited to, hydrogel pads, macroporous gel/media, dielectric media, pyrrole, polyethylene glycol (PEG), polyacrylamide (PA) as well as others. Such porous media further includes silica aerogels (i.e., silica gel, solgel, or SiO matrix), as well as aerogel/hydrogel combinations. Desirably, PA is any variation of polyacrylamide (e.g., acrylamide that is functionalized, activated, modified, or otherwise combined with any appropriate moiety) such as is known in the art. Similarly, preferably any other porous media according to the invention can be modified (e.g., functionalized, activated, or otherwise combined with any appropriate moiety).

Preferably according to the invention, the porous media is present on a substrate so as to constitute an array or matrix. According to the invention, the porous media is "present on a substrate" so as to constitute an array or matrix when it either is on a surface (e.g., a top surface as in FIG. 1), or where holes are created within, and preferably, either partially or all the way through the substrate, and the porous media is formed or placed in these holes so as to constitute the array. For instance, FIG. 2 depicts a sample array of the invention (other configurations also can be employed) from the top view wherein holes are created within and all the way through the substrate and the porous media is formed inside of or placed in these holes so as to constitute the array.

The "substrate" itself optionally is any solid substrate that can be employed in the invention, e.g., film, glass, Si, modified silicon, ceramic, plastic, resins, or any type of appropriate polymer such as (poly)tetrafluoroethylene, or (poly)vinylidenedifluoride. Preferred substrates according to the invention are glass and plastic. The solid substrate can be any shape or size, and can exist as a separate entity or as an integral part of any apparatus (e.g., bead, cuveffe, plate, vessel, and the like). It further is assumed that appropriate treatment of the solid substrate (e.g., glass) will be undertaken to provide adherence of polyacrylamide (or other medium) to the glass, e.g., with γ-methacry-oxypropyl-trimethoxysilane ("Bind Silane", Pharmacia), or other appropriate means. In particular, covalent linkage of polyacrylamide hydrogel to the solid substrate can be done as described in European Patent Application 0 226 470 (incorporated by reference). The solid substrate also optionally contains electronic circuitry used in the detection of bit molecules, or microfluidics used in the transport of macromolecules.

By "array" or "matrix" is meant an arrangement of locations (i.e., "microlocations") on the substrate. The locations can be arranged in two dimensional arrays, three dimensional arrays, or other matrix formats. The number of microlocations can range from one microlocation to a plurality of microlocations (e.g., from two to hundreds of thousands). A device thus can be designed to have as few as one microlocation (i.e., locations comprised of polyacrylamide or other porous media that can be addressed in the methods and apparatus of the invention) or as many as hundreds of thousands of microlocations present on a substrate.

Desirably an array is comprised of locations in rows and columns. It is not necessary according to the invention that these locations be separately addressable (e.g., as in cases when immunofluorescent detection of binding is employed), but in some cases, it may be preferable (e.g., in cases where electrical detection is used). Such a hydrogel array as contemplated herein is known in the art, and referred to by a variety of names (e.g., "gel pad array", "polyacrylamide array", etc.). The thickness and dimensions of the hydrogel and/or hydrogel arrays, and/or other arrays produced according to the invention can vary dependent upon the particular needs of the user. Microlocations can be of any shape, and preferably, are either round, square, or rectangular. Optionally, however, the microlocations will each have a thickness of less than about 50 microns, desirably a thickness of between about 2 and about 40 microns, even more preferably a thickness of between about 15 and about 30 microns, and optimally, will be about 25 microns thick. Furthermore, desirably the microlocations in an array are each from about 0.5 microns to about 5 centimeters, with a preferred size being about 5 to about 500 microns in size, particularly from about 50 to about 400 microns, and especially from about 100 to about 200 microns.

Thus, preferably a device of the invention comprises a plurality of microlocations, wherein the microlocations each comprise a first binding entity having known binding characteristics, and wherein the first binding entity present in one microlocation differs from the first binding entity present in other microlocations in a known and predetermined manner. Along these lines, desirably, the first binding entity is a probe, and the sample is nucleic acid.

Buffer

Preferably according to the invention, bioconjugation and introduction of sample molecules and reagents is done with use of a buffer. Its also desirable that buffer solution is present in the hydrogel pads prior to (e.g., from about 15 minutes to about 4 hours before), concurrent with (e.g., at about the same time as), and/or following (e.g., from about 15 minutes to about 4 hours after) introduction of the sample. Thus, desirably according to the invention, buffer is present on or surrounding the microlocation(s) when bioconjugation is attempted.

The buffer provides a medium in which the binding entities can move in the porous media present on the substrate. The buffer also provides a medium in which the reactions attempted can ensue (e.g., hybridization, single base extension, polymerization, exonuclease digestion, etc.). A buffer (or electrolyte) is a chemical solution that is resistant to a change in pH upon the addition of acid or alkali. Preferably according to the invention, a buffer is based on an inorganic salt (e.g., phosphate, carbonate, etc.), or an organic acid salt (e.g., acetate, citrate, succinate, glycine, maleate, etc.). Desirably, a buffer is one that can be employed in hybridization and/or polymerization and/or exonuclease digestion and/or washing conducted using the methods or devices of the invention. It may be preferable that more than one buffer be employed in the methods and devices of the invention. Any appropriate buffer can be employed (such as is known in the art) to accomplish bioconjugation (e.g., hybridization), and/or polymerization, and/or exonuclease digestion, and/or washing.

Application of the electric field in the present invention affects any biomolecules that are in the buffer solution. The electric field may, in some cases, similarly impact buffer ions that produce optimum pH conditions for the reactions attempted using the methods and devices of the invention. For instance, with application of a field of the appropriate strength, movement of the buffer ions toward and away from the assay microlocations can mediate the pH at those microlocations. Accordingly, with some applications, it is desirable that a pH sensor is located on the surface of the bioarray in close proximity to the assay microlocations. This allows feedback to be provided as to the pH at the microlocation following or concurrent with application of an electric field. Similarly, with this information on pH provided before, during, or after a reaction, the local pH can be adjusted as needed, and assay conditions can be optimized. Generally, it is preferable that buffers be employed which are able to maintain the pH with application of an electric field.

Electrodes

Desirably, a device according to the invention includes two or more electrodes adapted to receive charge, the two or more electrodes being separated from one another, from the microlocation(s), and from the buffer, but appropriately positioned so as to create an electric field in the microlocation(s) without creating current flow in the microlocation(s) when the two or more electrodes receive charge.

Thus, the electrodes employed in the invention are contactless electrodes. By "contactless" electrodes is meant electrodes which are employed to generate an electric field and that are not in contact with the buffer which surrounds or is present in the porous media, and in which the sample desirably is contained. The terms "separated from one another" mean "not in contact" (i.e., not physically touching). This is achieved according to the invention by an arrangement of electrodes, sample, and buffer such that movement of the sample through the porous media is by virtue of electric field-mediated transport alone. In particular, the contactless electrodes are employed to generate electric fields which manipulate the biomolecules in such a way as to increase the occurrence of the desired bioconjugation events, e.g., a DNA and/or DNA/RNA hybridization event. This manipulation is electrostatic manipulation.

By an "electrode" is meant a electrode biased either positively or negatively, operating in either a direct current mode (either continuous or pulse), or operating in an alternating current mode, which can affect or cause the electric field-mediated, non-electrophoretic transport of charged specific binding entities, reactants, or analytes to or from any location on the device, or in the sample solution.

Since the electrodes employed in the invention are contactless, many more options are available for the composition of the electrodes. For instance, the electrodes can be made of metals such as gold, silver, platinum, copper, and alloys, conductive metal oxides such as indium oxide, indium-tin oxide, zinc oxide, as well as other conductive materials such as carbon black, and conductive epoxy. Generally, however, it is desirable that the electrodes employed in the invention are made of any conductive medium, even materials that traditionally have not been employed for electrodes (e.g., conductive polymers).

Generally, the structure of the present invention comprises two or more electrodes (i.e., minimally, at least two electrodes). Optimally the maximum number of electrodes is not more than the number of array microlocations to which biomolecules would be attracted/repelled. Even more preferably, the structure comprises from two to ten electrodes.

Desirably the electrodes are used to generate an electric field in the region of a molecule whose movement is to be effected. The electrodes desirably possess either alternating current (AC) or direct current (DC) bias. These electrodes are not in contact with the buffer solution or the sample biomolecules, e.g., DNA, RNA, etc., which are being manipulated, but can be in contact with the substrate. Since biomolecules such as DNA, RNA, etc. are charged, the electric field can be used to affect the diffusion velocity of the molecules through the substrate. Thus, the sample can be made to diffuse into and out of test sites as many times as is necessary to obtain sufficient bioconjugation events, such as DNA hybridization. By comparison, preferably the substrate itself is inert to electrostatic influence and conducting of charge.

In particular, desirably the electrodes: (1) affect or cause the electric field-mediated transport of specific (charged) binding entities from any location; (2) concentrate and allow covalent or noncovalent attachment of the specific binding entities to their binding partners optionally present at specific microlocations; and (3) continue to actively function in the DC or AC mode after the attachment of specific binding entities so that other reactants and analytes can be transported to or from the microlocations.

Any appropriate size of the electrodes can be employed according to the invention. By comparison, the spacing between each of the two or more electrodes (e.g., "30" in FIGS. 1 and 3) and the buffer surrounding or contained in the porous media is very important, and can be termed the "electrode spacing". Preferably the electrode spacing is a distance that desirably ranges from about 1.5 nm at a minimum to about 5 cm at a maximum, and preferably ranges from about 1.5 nm to about 3 mm. Desirably the electrode spacing includes empty space (i.e., merely air, or a vacuum, with nothing additional present, apart from, optimally, buffer, the porous media and substrate, any probe present in the porous media, and/or any sample placed in the porous media, and/or other components of the hybridization cell). Thus, desirably, the electrode spacing can consist essentially of a mixture of merely one or more spaces of air or vacuum with nothing additional present inside, and one or more spaces of buffer, porous media and substrate, any probe present in the porous media, and/or any sample placed in the porous media, and/or other components of the hybridization cell.

According to the invention, preferably the electrodes are biased to enhance the diffusion of the sample binding entities into the porous media, or out of the porous media, and to enhance the spreading of sample across the whole volume of the porous media. This process desirably is repeated an appropriate number of times (i.e., "appropriate" to provide the desired hybridization or other bioconjugation event) with the use of an AC or DC bias to provide the sample (e.g., target DNA) with an optimal cross section of the binding entities (e.g., DNA probes) for bioconjugation (e.g., hybridization) to occur. In this way, the occurrence of bioconjugation events (including hybridization events) can be enhanced.

Preferably according to the invention, the device comprises at least two electrodes, and can comprise as many electrodes as is feasible, i.e., desirably from two to two hundred electrodes, and even more preferably, from two to ten electrodes. The electrodes can be positioned vis-à-vis the other electrodes, and vis-à-vis the substrate, in any conceivable fashion in which the devices of the invention can be constructed, and in which the methods of the invention can be carried out. For instance, at least one of the electrodes can be placed directly on a surface of the substrate, so long as it does not contact the buffer, and/or the sample contained in the buffer. In some instances, it may be necessary to construct the device such that the electrodes are moveable, and are positioned with respect to the substrate after the substrate has been appropriately positioned (e.g., in three-dimensional structures, wherein the substrate is placed in the center of the structure, and the electrodes essentially surround the substrate in all directions). With a very large number of electrodes, e.g., ten or more, it is desirable that the configuration of the electrodes approximate that of a cylinder or sphere in either one- or three-dimensions, with the substrate being placed preferably at about the center. However, basically any arrangement of electrodes and substrate that could be employed in the invention to obtain electrostatic movement/bioconjugation of molecules are herein contemplated, and are within the knowledge and level of skill of one skilled in the art to achieve.

In terms of particularly preferred configurations, the invention provides a device, desirably wherein:

(a) two electrodes are present, and the electrodes are on opposite sides of the substrate in a stacked arrangement;

(b) three electrodes are present, and the electrodes form a triangle in one plane, having a center in the plane, with the substrate located in the center;

(c) four electrodes are present, and the electrodes form a square in one plane, having a center in the plane, with the substrate located in the center;

(d) five electrodes are present, and the electrodes form a pentagon in one plane, having a center in the plane, with the substrate located in the center;

(e) five electrodes are present, and the electrodes form a three dimensional triangle, having a center in the triangle, with the substrate located in the center (i.e., desirably at the center of all three dimensions);

(f) six electrodes are present, and the electrodes form a hexagon in one plane, having a center in the plane, with the substrate located in the center; or (g) six electrodes are present, and the electrodes form a three dimensional square, having a center in the square, with the substrate located in the center (i.e., desirably at the center of all three dimensions of the square).

Voltage Source and Application of Charge

The device and methods of the invention desirably provide a source, e.g., preferably a voltage source, for providing charge to the electrodes. Such a source (i.e., a voltage source) must be able to provide either AC bias and/or DC bias to the electrode. Preferred voltage sources for supplying AC and DC bias include a standard power supply (i.e., a battery), and a transformer. Generally, to establish the electric field, from at least about 200 volts/cm to at least about 10,000 volts/cm must be delivered by the power supply.

It further is preferable according to the invention that the two or more electrodes optionally can be separately controlled by power sources. For instance, it may be desirable that bias is created by separately charging one electrode as opposed to others. It also may be preferable that charge be sequentially applied to the electrodes. In particular, it is preferred that the electrodes are controlled in such a way so as to produce a stirring motion, or cause a rotational motion. For instance, the electrodes can be individually turned on and off (e.g., in a series, in a random fashion, or in another fashion), the electrodes can be differentially charged so as to produce a field gradient, etc. This particularly is desirable since it will allow the biomolecules (i.e., sample molecules) to be moved throughout the entire array, and will maximize exposure of the probes to the targets. Such an approach is optimized particularly when the arrangement of the electrodes approximates a cylinder or sphere. It further may be desirable to charge the electrodes at different levels. This flexibility in control of the electrodes in creation of AC and/or DC bias further increases the flexibility of the methods and devices of the invention.

Advantages

The invention has certain advantages over those previously described. First, the need to restrict the material of the electrode to only biocompatible materials is eliminated since the electrodes desirably do not come into contact with the sample or buffer. This increases flexibility in electrode material selection. Second, the need for complicated designs, and micro- and nano-lithography to incorporate full contact electrodes in the array is also eliminated. This simplifies the manufacturing process and decreases cost. Third, since the electrodes do not come into contact with the sample, with the substrate, and/or with the buffer (if buffer is present), any unwanted or unexpected reaction between the electrodes and the sample, between the electrodes and the substrate, and between the electrodes and the buffer solution, is avoided. The probability of electrode degradation, and unwanted current flow, also is eliminated. Other advantages of the invention would be apparent to one skilled in the art in view of this specification disclosure.

Preferred Devices and Methods

Figure 1:
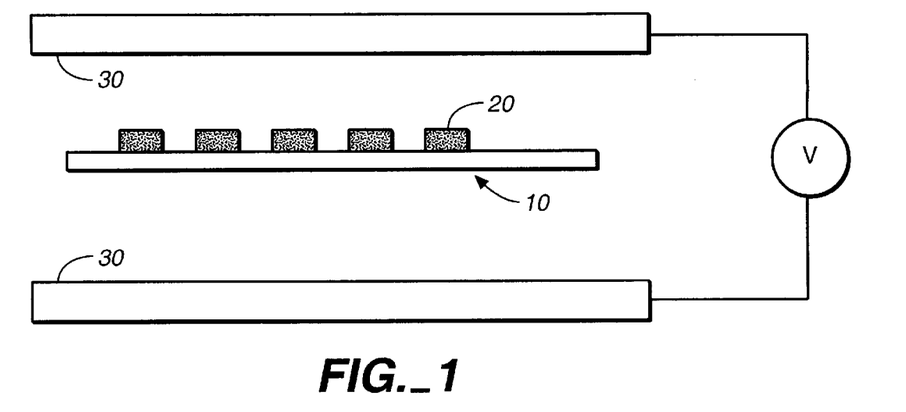
FIG. 1 depicts a preferred device of the invention wherein the porous media (i.e., here, hydrogel pads) present on a substrate (i.e., an array) are sandwiched between electrodes such that the electrodes do not physically contact the buffer surrounding the porous media or the porous media itself, but the electrodes are capable of creating within the buffer and the porous media an electric field. Numbers: 10, substrate; 20, porous media; 30, electrodes. Symbol: V, voltage source.
Figure 2:
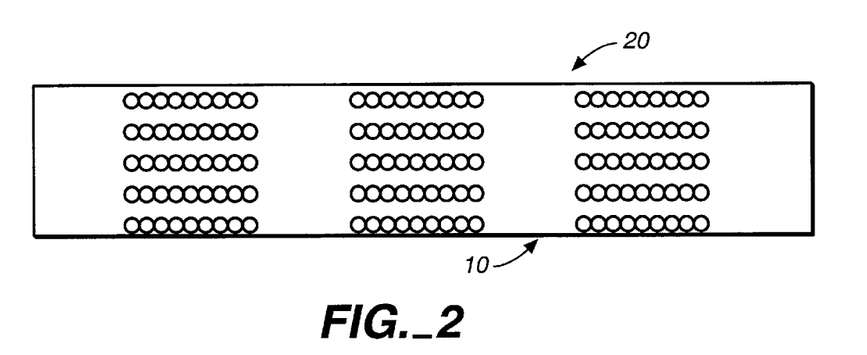
FIG. 2 depicts a sample array of the invention (other configurations also can be employed) from the top view wherein holes are created within and all the way through the substrate and the porous media is formed or placed in these holes so as to constitute the array. Numbers: 10, porous media; 20, substrate; 30, electrodes.
Figure 3:
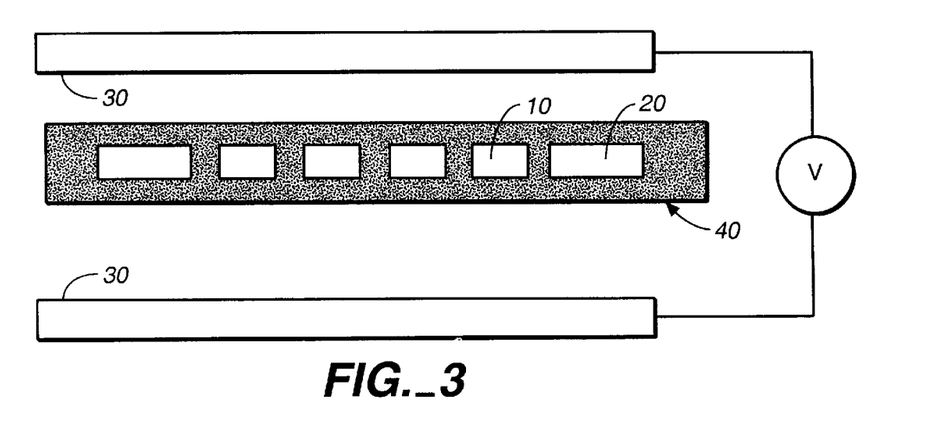
FIG. 3 depicts the array in FIG. 2 placed in a hybridization cell between two electrodes, as seen from a side view of a cross section through a row as seen in FIG. 2, wherein the porous media present on the substrate is placed inside a hybridization cell sandwiched between electrodes, such that the electrodes do not physically contact the buffer surrounding the porous media or the porous media itself, but the electrodes are capable of creating within the buffer and the porous media an electric field. Numbers: 10, porous media; 20, substrate; 30, electrodes; 40, hybridization cell. Symbol: V, voltage source.

Preferred devices according to the present invention and inherent advantages and uses are as described above, and can be further understood by referring to FIGS. 1–3 of the drawings, with like numerals being used for like and corresponding parts of the various drawings. Many other system configurations in the spirit and scope of the present invention can be employed, and would be apparent to those skilled in the art based on the specification disclosure.

Desirably, the preferred methods and devices of the invention can be used with any bioconjugation protocol, and especially with any hybridization protocol, e.g., "standard" hybridization, sequencing by hybridization, and the like. The invention can be employed wherein either the sample binding entity (e.g., DNA or the probe DNA) is either (a) adhered to the substrate, (b) not adhered to the substrate, (c) adhered (e.g., covalently bound) to the porous media, and/or (d) entrapped in (e.g., encapsulated by) the porous media.

When considered in terms of enhancing DNA hybridization events, in FIGS. 1 and 3, single strand DNA probes (e.g., oligonucleotide probes) or other binding entities desirably are either immobilized or merely placed (i.e., are not immobile) in a porous media present on a substrate.

The porous media present on the substrate then is either inserted into or is already present in a hybridization cell that contains the sample (e.g., as depicted in FIG. 3), or the sample is directly applied to the porous media (e.g., as for the arrangement in FIG. 1). The sample molecules (e.g., sample DNA) desirably are introduced into the system by placing the sample in contact with the porous media (e.g., hydrogel pads) or by merely adding them to a hybridization cell. Such contact can be brought about by any appropriate means. For instance, the sample (e.g., DNA) can be added, e.g., in a buffer solution. Preferably the introduction of the sample into the analysis system can be made prior to (e.g., from about 15 minutes to about 4 hours before), concurrent with (e.g., at about the same time as), or following (e.g., from about 15 minutes to about 4 hours after) the initiation of the electric field. The porous media present on the substrate is then inserted in between two or more electrodes, or two or more electrodes are placed at various locations with respect to the porous media (e.g. as where moveable electrodes are employed).

At this stage, the hybridization cell is then present between at least two electrodes (e.g., as depicted in FIGS. 1 and 3). To enhance hybridization and increase exposure of the probe to the sample target, the electrodes are turned on to generate an electric field by applying an alternating bias (i.e., using either AC or DC current). Desirably the electric field is applied in such a way that the molecules present in the sample (e.g., DNA molecules) are attracted towards the probes in the microlocations on the support medium, and are made to diffuse through the porous media so as to contact the binding entities (i.e., probes) present in the porous media. Because this increases the exposure of the binding entities, this should reduce the time period for hybridization, and also, increase the probability of hybridization. When the desired bioconjugation reaction is complete, the electrode potential can be reversed or altered to direct unbound sample binding entities in a direction away from the binding entities present at the microlocations. This should facilitate removal of the nonspecifically bound or nonbound sample and/or probe. This process of applying and reversing (or altering) the electric field can be repeated an appropriate number of times to increase the probability of specific bioconjugation (i.e., specific hybridization).

Thus, the preferred devices of the invention desirably can be employed in a method for bioconjugating binding entities. Preferably, this method is carried out in a device having one or a plurality of microlocation(s) present on a substrate, wherein the microlocation(s) comprise a first binding entity, and the method comprises the steps of:

(a) applying sample comprising one or more further binding entities to the microlocation(s); and (b) applying charge to the device to produce an electric field at the microlocation(s) without creating current flow in the microlocation(s), and such that the one or more further binding entities are transported to the first binding entities present in the microlocation(s) under conditions sufficient for bioconjugation to occur.

The method optionally can be carried out comprising the further step (c) of applying charge to the device to produce an electric field at the microlocation(s) without creating current flow in the microlocation(s), and such that the one or more further binding entities that are not bioconjugated with the first binding entities are transported away from the first binding entities in the microlocation(s). Optimally, steps (b) and (c) are repeated at least one time, and preferably, are repeated anywhere from one time to one hundred times.

In an especially preferred embodiment, desirably the method is carried out where the device comprises a plurality of microlocations. Preferably the microlocations each comprise a first binding entity having known binding characteristics, and the first binding entity present in one microlocation differs from the first binding entity present in other microlocations in a known and predetermined manner. Optimally, the method is carried out where the first binding entity is a probe, and the sample is nucleic acid.

There are two preliminary considerations that preferably are addressed prior to use of the methods and devices of the present invention: (1) sample preparation, and (2) probe and label design.

1. Sample Preparation:

The biological sample (e.g., especially a sample containing DNA or RNA) can be isolated by any of a variety of means known to those skilled in the art. For instance, blood samples can be taken from one or more individuals. High molecular weight DNA can be prepared by using Triton X-100 followed by Proteinase K and RNAse treatment (see, e.g., Bell et al., *Proc. Natl. Acad. Sci.*, 78 5759–5763 (1981)). In vitro amplification of the DNA template then can be carried out (if necessary or desired), for instance, using PCR or isothermal strand displacement amplification. In particular, it is desirable that the primers used for PCR conform as much as is practicable to accepted parameters of favorable PCR primer design (e.g., as set forth in Taylor et al., *Methods Mol. Biol.*, 70, 273–278 (1997)). "Amplified" means that many accurate DNA copies are made from the primary DNA sample. This amplified DNA will be referred to as "sample". Desirably the DNA sample is rendered single stranded prior to use in the methods and/or devices of the invention by any appropriate means, e.g., heating, selective degradation of a single strand, etc.

When the biological sample is other than DNA or RNA (e.g., is protein or polypeptide) any appropriate means of isolation and sample preparation can be employed such as is known in the art.

2. Probe and Label Design:

In particular, preferably the invention is used with a "probe array", where the probe/primers are designed so that they are attached at their 5' ends to either a porous media or to a solid support. Preferably the probes are attached in arrays. The oligonucleotides can be synthesized in situ, or desirably, are presynthesized and attached to a support. Any means of attachment are contemplated according to the invention. For instance, the DNA can be fixated to the substrate by conjugating the reagents for synthesis with a specific binding protein or other similar substance and coating the surface of the support with the binding counterpart (e.g., biotin/streptavidin, nucleic acid/nucleic acid binding protein, etc.). In particular, preferably the probe/primers are attached by means of a hydrogel support. In an array according to the invention, desirably the sequence and/or position of every probe on the array is known, such that the probe array can be employed in sequencing and diagnostic applications, in forensics analyses, determinations of paternity, veterinary applications (e.g., thoroughbred testing), and the like.

In terms of substrate anchoring, preferably the probe is capable of being anchored at its 5' end to a solid substrate or permeable material present thereon (e.g., hydrogel pads). For example, this can be accomplished chemically, or alternately, through a biotin-streptavidin interaction.

Any of the conventionally used methods of labeling (e.g., radioisotopes, enzymic, fluorescent labels, redox or other electrochemical labels, chemiluminescent labels, haptenic labels such as biotin, or other labels such as ligands, antigens, and the like) can be used according to the present invention and as set out, for instance, in: U.S. Pat. Nos. 4,563,417, 4,581,333 and 4,582,789; EP Applications 119448 and 144914; and Prober et al., Science, 238, 336–340 (1987). For instance, a probe can be employed which includes a detectable label, label can be incorporated into a probe DNA hybrid (e.g., by single base extension), and/or probe DNA hybrids can be detected following their hybridization.

When a probe is employed for labeling, the probe desirably is designed to embody certain characteristics in terms of composition, substrate anchoring, and sequence. In particular, desirably the probe is composed of DNA. In one embodiment, preferably the one or more of the first five of the 5' bases (and desirably, the first three 5' bases) comprise unlabeled deoxyuridine triphosphate (dUTP), and this is followed by one or more of the next five bases (and desirably, the next four bases) which comprise detection labeled dUTP bases. The series of dUTP bases constitutes the "leader". Examples of detection-labeled dUTP are radioactive isotopes, such as $^{32}$P, $^{33}$P, $^{35}$S, fluorescence-conjugated dUTP, such as Cy3-dUTP, or alternatively biotin-dUTP which would allow subsequent fluorescent conjugation with strepavidin-conjugated fluorochromes. Means of probe labeling, and other means of labeling to detect hybridization and other bioconjugation events are well known in the art. Any appropriate means can be employed in the methods and devices according to the invention.

The steps employed with use of the methods and device of the invention generally comprise (a) hybridization, (b) optionally extension, and (c) detection.

A. Hybridization: Generally, according to the invention, hybridization is carried out by standard means, with the additional requirement that an electric field be applied as previously described to facilitate specific binding of binding entities, and to facilitate the reversal of nonspecific binding, and removal of unreacted (i.e., nonspecifically bound) sample molecules. Reaction conditions for bioconjugation include provision of appropriate salts and buffers with each enzyme incubation. The reaction conditions for hybridization desirably are maintained such that the oligonucleotide probes stably and specifically hybridize to the target polynucleotide.

The reaction conditions for polymerization (i.e., during the sequencing platform) preferably are maintained such that the 3'-terminus of the oligonucleotide probes are extended by the addition of modified DNA bases (i.e., including the interrogation nucleotide).

According to the invention, a hybridization reaction mixture is maintained under hybridizing conditions for a time period sufficient for a probe (e.g., a polynucleotide probe) to hybridize to complementary nucleic acid sequences present in the sample to form a hybridization product, e.g., a complex of polynucleotide probe and target nucleic acid. Such "hybridizing conditions" (e.g., "hybridization conditions") indicates subjecting a hybridization reaction mixture to time, temperature, and pH conditions needed to allow the probe to hybridize with the nucleic acid sequence of the sample. Such time, temperature, and pH conditions are well known in the art, and depend, for instance, on the length and composition (e.g., guanidine and cytosine content) of the polynucleotide probe to be hybridized, the degree of complementarity between the polynucleotide probe and the sample, the stringency of the hybridization employed, and the presence of salts or additional reagents in the hybridization mixture such as may affect the kinetics of the hybridization.

As defined herein, "stably" (or stable) hybridizing means that the hybridization desirably has a $T_m$ greater than the temperature under which the hybridization is to be carried out (i.e., typically from about 20° C. to about 40° C.). "Specific" hybridization means that the length and/or sequence complexity of the oligonucleotide probes employed for hybridization is/are sufficient to prevent any non-desirable spurious hybridization such as might occur between sequences that are only partially complementary.

Typical hybridization conditions include the use of solutions buffered to pH values ranging from about 4 to about 9, hybridization temperatures ranging from about 18° C. to about 70° C., and for time periods ranging from about 0.5 seconds to 24 hours. Hybridization preferably is carried out for from about 15 to about 30 minutes at room temperature in a solution that comprises about 1.5 M NaCl and 10 mM EDTA, although other hybridization conditions also desirably can be employed.

Hybridization desirably is carried out by incubating the probe and sample together in an aqueous solution (e.g., in a buffer solution) under the influence of an electric field. The relative quantity of sample and probe can be optimized empirically (e.g., as is known in the art) to ensure that the hybridization of the hybridizing strand to the probe is favored over the hybridization of the hybridizing strand to the nonhybridizing strand, i.e., to avoid the sample re-assembling its two strands. This reaction mixture (or a mixture containing the sample molecules alone) desirably is heated to approximately 95° C. for about 1 to about 2 minutes in order to cause the 2 strands of the sample to displace from one another (called "melting"). The heated mixture preferably is allowed to cool to about room temperature, and then is incubated, preferably at about room temperature, for at least from about 10 seconds to about 2 hours, and desirably for at least about 10 seconds to about 5 minutes, in the presence of an electric field in order to effect the hybridization of the probe to the hybridizing strand of the DNA sample. Optionally, the hybridization temperature can be increased or decreased from room temperature. Removal of nonbound or nonspecifically bound molecules can be effected (as previously described) by either reversing or otherwise altering the electric field. If desired, washing can optionally also be carried out. More preferably, however, the application of the electric field, followed by the reversal or other alteration of the electric field, is repeated at least one time to facilitate specific hybridization.

If the cooled mixture optionally is washed to remove unhybridized DNA from the mixture, then the wash desirably is accomplished by successive incubations in wash solution (e.g., as is well known in the art), wherein fresh wash solution is employed for each wash. Alternately the wash preferably is accomplished by continuous flow of fresh wash solution over the hybridized DNA. It further may be desirable that washing be carried out, as described above, with application (i.e., reversal or other alteration) of the electric field.

Typical characteristics of washing include a temperature of approximately 65° C., a low salt concentration, and the presence of a detergent such as sodium dodecyl sulfate. However, wash conditions can vary depending on many factors that have been well described in the art, e.g., probe length, probe composition, etc. Furthermore, when washing is applied in conjunction with use of an electric field, it may be desirable to carry out the wash at room temperature, and using a higher salt concentration (or even the same buffer as is employed for hybridization).

B. Single Base Extension: Optionally, according to the invention, probe and sample can be hybridized (and optionally washed) as described above, and then single base extension performed (i.e., such as has been described in the art). For instance, the probe desirably is immobilized at its 5' end, hybridized to the sample as described above, then incubated with a DNA polymerase (or other appropriate enzyme) in the presence of dideoxynucleotide triphosphates (ddNTPs, or any other appropriate chain terminating nucleotide) in a specific combination. Incubation times are typically short (e.g., from 0.5 to 5 minutes) and done at a temperature of about 37° C. The reaction will allow incorporation and extension of the probe by one base (i.e., a ddNTP base or other chain terminating base) if (and only if) a particular base in the complementary, sample strand is present. Following hybridization and, optionally, washing, detection of extended probes is performed. Therefore, the presence of detection-tagged probes at the original site of immobilization identifies the queried base on the sample strand as being complementary to the ddNTP (or ddNTPs) incubated in the DNA polymerase step.

A characteristic of some DNA polymerases is referred to as exonuclease activity. Thus the same enzyme which elongates (polymerase) DNA can, under certain conditions, also degrade (exonuclease) DNA. The polymerase used in single base extension desirably should have little or no exonuclease activity. Sequenase (Amersham) and Exo (−) Pfu polymerase (New England Biolabs) are examples of exonuclease activity-free DNA polymerases.

Under certain circumstances, incubating the polymerization mixture at an elevated (>37° C.) temperature could facilitate the reaction which incorporates the ddNTP into the probe. The elevated temperature would serve to effect a slight separation of the DNA strands, allowing DNA polymerase better access to the reaction site at the 3' end of the probe. These elevated temperature polymerase reactions optionally could be performed with thermostable Sequenase (Amersham) or the previously mentioned Exo (−) Pfu.

C. Detection: The substrate locations where probes were initially immobilized are assayed for the presence of detection-tagged bases, detection-tagged hybrids, etc. For example, if fluorescent bases are used for labeling, the area can be assayed for the presence of fluorescence by laser scanning microscopy.

The following example further illustrates the present invention but, of course, should not be construed as in any way limiting its scope.

EXAMPLE

Theoretical Underpinnings of the Invention

The field-enhanced hybridization of this invention is based on simple electrostatics. Generally, a charged particle has an electrostatic force towards the source of the opposite polarity when in an electric field. The strength of the electric field is described by the equation $V=Ed$, where V is the bias applied to the electrodes, E is the resultant electric field, and d is the separation between the electrodes. The size of the electrodes is irrelevant. This principle has been used in other applications, a few examples of which are: cathode ray tubes, ink jet printers, and flow cytometers for sorting. All these applications use a principle that involves the electrostatic deflection of charged particles.

Namely, for the flow cytometer, charged drops pass through two high voltage deflection plates and are attracted towards the plate of opposite polarity. The amount of deflection is dependent on the size of the drop, the strength of the electric field, and the amount of charge in the drop. In this way, two separate populations can be sorted.

In an inkjet printer, the ink droplets are ionized, and are electrostatically deflected by the appropriate field to create the desired pattern. In cathode ray tubes, the electron beams from the cathodes are electrostatically deflected the appropriate amount to hit the proper phosphor pixel in order to produce the desired pattern.

Similarly in the present invention, a bias is applied to the electrodes in such a way that the charged biomolecule (e.g., DNA) feels an electrostatic force directing it towards the probes, or towards the porous media containing the probes. Thus, according to the invention, through the application of electrostatic force, the direction of motion of a charged biomolecule can be manipulated. This application of electrostatic force to enhance hybridization has previously been unrecognized.

All of the references cited herein are hereby incorporated in their entireties by reference.

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed is:

1. A device for enhancing DNA hybridization comprising:
   (a) a substrate;
   (b) one or a plurality of microlocation(s) each microblocation comprising a DNA probe present on said substrate;
   (c) a buffer present on or surrounding said microlocation(s);
   (d) two or more electrodes adapted to receive charge, said two or more electrodes being separated from one another, from said microlocation(s), and from said buffer, but appropriately positioned so as to create an electric field in said microlocation(s) without creating current flow in said microlocation(s) when said two or more electrodes receive charge; and
   (e) an electrical source operatively associated with the electrodes for providing charge to said electrodes.

2. The device of claim 1, wherein said microlocation(s) comprise a porous media.

3. The device of claim 1, wherein the distance between said two or more electrodes and said buffer is each from about 1.5 nanometers to about 5 centimeters.

4. The device of claim 1, wherein from two to ten electrodes are present.

5. The device of claim 1, wherein more than two electrodes are present, and said electrodes are in a configuration that approximates that of a cylinder or sphere.

6. The device of claim 1, wherein:

(a) two electrodes are present, and said electrodes are on opposite sides of said substrate in a stacked arrangement;

(b) three electrodes are present, and said electrodes form a triangle in one plane, having a center in said plane, with said substrate located in said center;

(c) four electrodes are present, and said electrodes form a square in one plane, having a center in said plane, with said substrate located in said center;

(d) five electrodes are present, and said electrodes form a pentagon in one plane, having a center in said plane, with said substrate located in said center;

(e) five electrodes are present, and said electrodes form a three dimensional triangle, having a center in said triangle, with said substrate located in said center;

(f) six electrodes are present, and said electrodes form a hexagon in one plane, having a center in said plane, with said substrate located in said center; or (g) six electrodes are present, and said electrodes form a three dimensional square, having a center in said square, with said substrate located in said center.

7. A device adapted for enhancing DNA hybridization comprising:

(a) a substrate;

(b) one or a plurality of microlocation(s) present on said substrate, said microlocation(s) each comprising a DNA probe;

(c) a liquid dispensing source for applying sample comprising one or more further binding entities to said microlocation(s);

(d) a buffer present on or surrounding said microlocation(s);

(e) a first electrode adapted to receive charge;

(f) one or more other electrode(s) adapted to receive charge; and (g) a an electrical source operatively associated with the electrodes for providing charge to said first or said one or more other electrode(s), said first and said one or more other electrode(s) being separated from one another, from said microlocation(s), and from said buffer, but appropriately positioned so as to create an electric field in said microlocation(s) without creating current flow in said microlocations when said two or more electrodes receive charge.

8. The device of claim 7, wherein said microlocation(s) comprise a porous media.

9. The device of claim 7, wherein the distance between said first electrode and said substrate, and between said one or more other electrode(s) and said substrate, is each from about 1.5 nanometers to about 5 centimeters.

10. The device of claim 7 comprising a plurality of microlocations, wherein said microlocations each comprise a first binding entity having known binding characteristics, and wherein the first binding entity present in one microlocation differs from the first binding entity present in other microlocations in a known and predetermined manner.

11. The device of claim 7, wherein said first binding entity is a probe, and said sample is nucleic acid.

12. The device of claim 7, wherein from two to ten electrodes are present.

13. The device of claim 7, wherein more than two electrodes are present, and said electrodes are in a configuration that approximates that of a cylinder or sphere.

14. The device of claim 7, wherein:

(a) two electrodes are present, and said electrodes are on opposite sides of said substrate in a stacked arrangement;

(b) three electrodes are present, and said electrodes form a triangle in one plane, having a center in said plane, with said substrate located in said center;

(c) four electrodes are present, and said electrodes form a square in one plane, having a center in said plane, with said substrate located in said center;

(d) five electrodes are present, and said electrodes form a pentagon in one plane, having a center in said plane, with said substrate located in said center;

(e) five electrodes are present, and said electrodes form a three dimensional triangle, having a center in said triangle, with said substrate located in said center;

(f) six electrodes are present, and said electrodes form a hexagon in one plane, having a center in said plane, with said substrate located in said center; or (g) six electrodes are present, and said electrodes form a three dimensional square, having a center in said square, with said substrate located in said center.

* * * * *